United States Patent [19]

Pereira Da Luz

[11] 4,275,155

[45] Jun. 23, 1981

[54] MANUFACTURE OF AMINOGLYCOSIDE ANTIBIOTICS

[76] Inventor: Artur Pereira Da Luz, Avenida Gomes Pereira, 74,, 1500 Lisboa, Portugal

[21] Appl. No.: 67,528

[22] Filed: Aug. 16, 1979

[30] Foreign Application Priority Data

Nov. 24, 1978 [ES] Spain .................................. 475.393

[51] Int. Cl.$^3$ ............................................. C12P 19/48
[52] U.S. Cl. ..................................... 435/80; 435/867
[58] Field of Search .......................................... 435/80

[56] References Cited

U.S. PATENT DOCUMENTS 3,972,930  8/1976  Daum et al. ........................ 435/80

Primary Examiner—Alvin E. Tanenholtz
Attorney, Agent, or Firm—Cushman, Darby & Cushman

[57] ABSTRACT

A process for the production of gentamicins or more specifically a mixture of gentamicins $C_1$, $C_2$ and $C_{1a}$ by the aerobic fermentation of a new species *Micromonospora scalabitana* closely related to *Micromonospora narashinoensis* in suitable medium containing assimilable sources of carbon and nitrogen, calcium carbonate and several trace elements.

6 Claims, 1 Drawing Figure

FIG. 1

1. *Micromonospora* *purpurea* ATCC 15835
2. *Micromonospora* *scalabitana* var. *rubra*
3. Gentamicin (control)
4. *Micromonospora* *purpurea* N.R.R.L. 2953
5. *Micromonospora* *scalabitana* var. *pallida*

MANUFACTURE OF AMINOGLYCOSIDE ANTIBIOTICS

This invention relates to a novel method of manufacturing aminoglycoside antibiotics by fermentation using a new variety of microorganisms of the genus *Micromonospora*. More particularly, this invention deals with methods of producing gentamicins with a new species *Micromonospora scalabitana*. Cultures of the living microorganism were deposited at the American Type Culture Collection, Rockville, Maryland, USA, and were assigned the number ATCC 31435.

In the course of screening for antibiotics soil samples of Portugal, a beautiful red microorganism was isolated from a soil sample from the plains of Santarem, a city that in Roman times was called Scalabis. It was clear from the first tests that this microorganism was an antibiotic producer and that the metabolite was active against gram positive and gram negative microorganisms. These observations lead to its extensive study.

Microscopic examination revealed long branched mycelium with a few spores. First, it was considered a strain of Streptomyces but later it was established that it was a strain of Micromonospora and named *Micromonospora scalabitana*. The antibiotic produced was found to be identical with components of the gentamicin group by thin layer chromatography.

*Micromonospora scalabitana* was carefully tested and compared with other micromonosporas, especially those producing gentamicin. *Microscopic examination* of cultures shows that the microorganism produces a long branched mycelium of $0.5-0.7\mu$ in diameter. One week old or older cultures grown on special agar media contain round and ellipsoidal spores located on short or long sporophores. Some sporophores can be so short, that they seem to be sessile or almost sessile. Three day old cultures in broth grown in shake flasks contain many chlamydosphores. This microscopical picture and spore formation is very similar to that of young cultures of *M. chalcea* ATCC 12452 and *M. sagamiensis* ATCC 21803. Older cultures of *M. chalcea* and *M. sagamiensis* have overabundance of spores, while the number of spores produced by *M. scalabitana* remains modest and in characteristic configuration. A comparision with *M. purpurea* ATCC 15835 and N.R.R.L. 2953 was attempted, but both these strains are such poor spore formers that a meaningful comparison was not possible.

Growth on various culture media: *Micromonospora scalabitana* grows on many solid and in many liquid media. Growth and colony formation on solid media is quite characteristic. First there is a pin point size colony, which grows and changes into a small globule. The globule grows, increases in size and, when broken, it can be seen that it is a vesicle filled wih liquid. Additional growth and partial dessication cause flattening. In the center the growth stops but it continues growing on the bottom and edges, where the supply of nutrients is good. Growth, dessication and spreading cause: flattening, folding and cracking. These and other physical and metabolic processes cause formation of various colonial forms, some very bizzare or artistic: flat or plicate, tiny or giant, shaped as stars, flowers, etc. The growth is very slow.

*Micromonospora scalabitana* produces a red somatic pigment. It can be of various shades depending on composition of the media, pH, age of the culture, temperature of incubation and storage temperature. No agar-diffuseable pigment was observed. Like all other micromonosporas, *M. scalabitana* mutates very easily. Spontaneously, as well as after exposure to mutagenic agents, it can give mutants of many colors, ranging from colorless to black and of many colors and shades in-between. It also produces mutants with changed metabolism, requiring special nutrients and producing an altered antibiotic pattern. Some of these mutants have abundance of spores, others paucity of spores.

As mentioned above, the original strain of *M. scalabitana* was red, forming few spores. Following mutations and selective isolation many other characteristic strains were isolated. To eliminate confusion, just for practical reasons, that new characteristic was included into the name and hence not only *M. scalabitana* var. rubra (the type strain) exists, but also *M. scalabitana* var. pallida, var. aurantiaca, var. salmonicolor, var. coelicolor, var. ferruginosa, var. brunea, var. sporogenes and var. asporogenes.

Spore formation is very light or absent among colorless and light-colored strains, quite the opposite, darker or darkening strains have often, but not always, abundance of spores.

For the description of the pigments, standard color charts were not used. With all those variations such studies are, not only impractical, but often misleading. All those pigments are very changeable and they have different hues caused by small differences in media composition, pH, nutrients, temperature of incubation, age of culture, etc. In general, younger cultures, especially those grown at lower temperatures and pH below 7, are lighter and brighter. Cultures grown in alcaline conditions, at higher temperatures and with longer incubations, are of darker shade and often form dark pigments (brown, gray, purple, black and green).

*M. scalabitana* grows well under aerobic conditions in the temperature range $25°-38°$ C. It also grows under lower temperatures, but more slowly. It even continues growing in the refrigerator at $4°$ C. For such cultures in a refrigerator it is necessary to initiate growth first. For example: inoculated agar plates are left overnight standing on a laboratory table at room temperature. Next day the growth is not visible but if the plates are then left standing in the refrigerator the growth very slowly develops. For a fullgrown culture 5-6 months incubation in the refrigerator is necessary. Dark pigments were never observed under those cold conditions, only light colored pigments develop.

Two strains of *M. scalabitana* were selected and deposited in the American Type Culture Collection. They are *M. scalabitana* var. rubra ATCC 31435 and *M. scalabitana* var. sporogenes. ATCC 31436.

The media used for *Micromonospora scalabitana* studies were the following:
Bennett's agar
Emerson's agar
Czapek-Dox agar (Difco)
Gelatin (Difco)
Antibiotic agar no 11 (Difco)
Nutrient agar (Difco)
Glucose yeast extract agar
Glucose asparagine agar
NZ Amine glucose agar
Peptone iron agar (Difco)
Tryptose broth (Difco)
Tryptose agar The precise composition of these media is generally well known and described in various manuals and text books as well as in the Media Section of the A.T.C.C. catalogue.

In addition, many other media prepared and described for micromonospora studies (see for instance G. M. Luedeman, U.S. Pat. No. 3091572) were used as for example:

Luedeman's micromonospora basal medium:

| Broth: | Beef extract | 0.3% |
|---|---|---|
| | Tryptose | 0.5% |
| | Yeast extract | 0.5% |
| | Dextrose | 0.1% |
| | Soluble starch | 2.4% |

They are dissolved in deionized water, the pH is adjusted to 7.2–7.3 and sterilized in autoclave at 121° C.

Agar: To the composition described above is added agar 1.5% (Difco), the pH is adujsted to 7.2 and sterilized in the autoclave at 121° C.

Medium for preparation of washed mycelium (Luedeman-Brodsky) (G. M. Luedeman and B. C. Brodsky, Antimicrob. Ag. and Chemoth. (1963), 116)

| NZ Amine type A (Sheffield) | 0.5% |
|---|---|
| Yeast extract (Difco) | 0.5% |
| Soluble starch (Difco) | 2.0% |
| Dextrose (Merck) | 0.1% |
| Calcium carbonate (Merck) | 0.1% |

They are dissolved in deionized water, pH adjusted to 7.2 and sterilized in autoclave at 121° C.

It should be noted that in this and other media NZ Amine is a trade mark of the Sheffield Chemical Co., Norwich, N.Y., U.S.A. and Difco and Merck mean, respectively, reagents of the Difco Laboratories Inc., Detroit, Mich., U.S.A. and of E. Merck, Darmstadt, German Federal Republic.

Basal medium for carbohydrate utilization studies (Luedeman) (G. M. Luedeman, Trans. N.Y. Acad. Sci. 33 (2), 207 (1971)

| Yeast extract (Difco) | 0.5% |
|---|---|
| Calcium carbonate (Merck) | 0.1% |
| Agar (Difco) | 1.5% |
| Distilled water up to | 100% |
| sterilized in autoclave at 121° C. | |

The carbohydrates are prepared separately, autoclaved separately in dry state and mixed with melted agar to obtain a final concentration of 1%.

Agar for spore formation studies:

| Dextrose (Merck) | 1.0% |
|---|---|
| Yeast extract (Difco) | 0.5% |
| Agar (Difco) | 1.5% |

-continued

| Calcium carbonate (Merck) | 0.1% |
|---|---|

They are dissolved or suspended in deionized water, the pH adjusted to 7.2 and sterilized in autoclave at 121° C.

Slightly less favorable results were obtained with the agar described as the A.T.C.C. Medium no 5.

Potato slices—They were prepared in the usual way using local white potatoes as the starting material. After autoclaving the pH of plain potatoes was 5.4, which is lower than the pH of the potatoes used by Luedeman. When the surface of the potatoes was slightly covered with calcium carbonate the pH on the surface was 6.8.

*Micromonospora scalabitana* was carefully studied using all the media described. Whenever and wherever it was possible, *M. scalabitana* was compared with known micromonosporas, especially those producing the gentamicin complex. Those strains most often used for comparison were the following: *M. purpurea* A.T.C.C. 15835, *M. purpurea* N.R.R.L. 2953, *M. chalcea* ATCC 12452, the red variant of the A.T.C.C. strain number 12452 isolated in our laboratory, *M. sagamiensis*, ATCC 21803 and a recently isolated strain of *M. echinospora* var. pallida. Comparison of growth and pigment formation of those strains are shown in Table I.

Sodium chloride tolerance was tested on Ludeman's micromonospora basal medium agar. Various concentrations of sodium chloride were added to the melted agar and after solidification various strains of micromonospora were inoculated on the surface and incubated at 32° C. for 7 days. The results are shown in Table II.

*Micromonospora chalcea* was the most resistant with light growth even at 5% concentration. *M. purpurea* and *M. echinospora* were able to grow at 3% concentration of sodium chloride. *M. scalabitana* was the most sensitive. It tolerated well concentrations of NaCl of 1% or less. There was only a scant growth at 2% and absolutely no growth at higher concentrations.

Influence of pH was tested on the same Luedeman's basal medium and the pH was adjusted to desirable degrees with hydrochloric acid. Melted agar was poured in Petri dishes and, after solidification, the agar surface was inoculated with various strains of micromonospora. All plates were incubated for seven days at 32° C. and the results are tabulated in the Table III.

Again *M. chalcea* was the most resistant and able to grow even at pH 5.8 and there was luxurious growth on plates at pH higher than 6. Both strains of *M. purpurea* and *M. echinospora* and both strains of *M. sagamiensis* tolerated a pH of 6.1. *M. scalabitana* was, again, the most sensitive. There was medium growth at pH 6.5 and no growth at lower pH.

Growth on potato plugs was slightly different from what was reported by Luedeman. The reason was very simple. Luedeman used American white potatoes that after sterilization had pH 5.8–6.2 on the surface. Those used here were of Portuguese origin and the pH was 5.4 on the surface after sterilization. When this acidity was eliminated with calcium carbonate

TABLE 1

| Medium: | M. purpurea ATCO 15835 | M. purpurea NRRL 2953 | M. echinospora var. pallida | M. scalabitana var. rubra ATCC 31435 | M. scalabitana var. pallida | M. chalcea ATCO 12452 var. aurantiaca | M. chalcea ATCO 12452 var. rubra | M. sagamiensis ATCO 21803 |
|---|---|---|---|---|---|---|---|---|
| Czapek-Dox agar | Gr. fair | Gr. fair | Gr. fair | Gr. fair | Gr. fair | Gr. fair | Gr. fair | Gr. fair |
| | C. lt. orange | C. Lt. brown | C. Lt. orange | C. lt. brown | C. Colorless | C. orange | C. orange-red | C. apricot |

TABLE 1-continued

| Medium: | M. purpurea ATCO 15835 | M. purpurea NRRL 2953 | M. echinospora var. pallida | M. scalabitana var. rubra ATCC 31435 | M. scalabitana var. pallida | M. chalcea ATCO 12452 var. aurantiaca | M. chalcea ATCO 12452 var. rubra | M. sagamiensis ATCO 21803 |
|---|---|---|---|---|---|---|---|---|
| Glucose-yeast extract agar | D.p. O Gr. good C. purplish darkening | D.p. O Gr. good C. purple later black | D.p. O Gr. good C. Lt orange darkening | D.P. O Gr. good C. Red-brown | D.p. O Gr. good C. Colorless | D.p. O gr. good C. bright orange | D.p. O Gr. good C. orange-red | D.p. O Gr. good C. bright orange |
| Glucose-aspargine agar | D.p. O Gr. poor C. Bluish-purple | D.p. O Gr. poor C. reddish-purple | D.p. O Gr. poor C. bluish-purple | D.p. O Gr. poor C. brown | D.p. O Gr. poor C. colorless | D.p. O Gr. poor C. deep orange | D.p. O Gr. poor C. red | D.p. O Gr. poor C. brick red |
| Antibiotic agar #11 | D.p. O Gr. poor to fair C. Lt. orange | D.p. O Gr. poor to fair C.Lt. orange later gray | D.p. O Gr. fair C.Lt. orange graying | D.p. O Gr. poor to fair C. Red brown | D.p. O Gr. poor C. colorless | D.p. O Gr. poor C.orange | D.p. O Gr. poor C. red | D.p. O Gr. poor O. orange |
| Pepton-iron agar | D.p. O Gr. poor to fair C. lt. orange | D.p. O Gr. poor to fair C. colorless | D.p. lt. gray-brownish gr. poor C. Colorless | D.p. O Gr. poor to fair C. reddish-brown | D.p. O Gr. poor C. Colorless | D.p. O Gr. poor C. Lt. orange | D.p. O Gr. poor C. Lt. red | D.p. O Gr. poor C. Lt. orange |
| Amine-glucose agar | Dp. O Gr. fair C. orange-brown edge | D.p. O Gr. fair C. brown darkening | D.p. O Gr. fair to red C. brown later purplish | D.p. O Gr. fair C. dark red-brown | D.p. O Gr. fair C. Colorless | D.p. O Gr. fair C. brown-red | D.p. O Gr. fair C. dark red-brown | D.p. O Gr. fair C. colorless |
| Tryptose agar | D.p. O Gr. fair C. bright orange | D.p. O Gr. fair C. orange | D.p. O Gr. fair C. orange | D.p. O Gr. fair C. raspberry red | D.p. O Gr. fair C. Colorless | D.p. O Gr. fair C. orange | D.p. O Gr. fair C. red | D.p. O Gr. fair C. orange greenish |
| Emerson's agar | D.p. O Gr. good C. reddish orange | D.p. O Gr. good C. reddish orange | D.p. O Gr. good C. brown | D.p. O Gr. good C. Raspberry red | D.p. O Gr. good C. Colorless | D.p. O Gr. good C. lt. brown | D.p. O Gr. good C. darkening red | D.p. O Gr. good C. orange |
| Bennett's agar | D.p. O Gr. good C. dusty orange | D.p. O Gr. good C. reddish orange | D.p. O Gr. good C. brown | D.p. O Gr. good C. raspberry red | D.p. O Gr. good C. colorless | D.p. O Gr. good C. terra cotta | D.p. O Gr. good C. red | D.p. O Gr. good C. orange |
| Luedeman's basal agar | D.p. O Gr. luxurious C. reddish orange | D.p. O Gr. luxurious C. orange later purple | D.p. O Gr. luxurious C. orange later brown | D.p. O Gr. luxurious C. darkening red | D.p. O Gr. luxurious C. colorless | D.p. O Gr. very good C. darker terra cotta | D.p. O Gr. very good C. darkening red | D.p. O Gr. very good C. orange brown |
| Gelatin | D.p. O liquefied | D.p. O liquefied | D.p. lt.brown liquefied | D.p. O liquefied | D.p. O liquefied | D.p. O liquefied | D.p. O liquefied | D.p. O liquefied |

NOTE: Abreviations:
Gr. = growth
C. = color
D.p. = difusible pigment
lt. = light

TABLE II

NaCl tolerance (on agar)
Comparison of six strains of various Micromonosporas

| Sodium chloride 1% | M. purpurea ATCC 15835 | M. purpurea NRRL 2953 | M. scalabitana var. rubra ATCC 31435 | M. scalabitana var. sporogenes ATCC 31436 | M. chalcea ATCC 12452 | M. echinospora var. pallida |
|---|---|---|---|---|---|---|
| 0 | +++ | +++ | +++ | +++ | +++ | +++ |
| 1 | +++ | +++ | +++ | +++ | +++ | +++ |
| 2 | +++ | +++ | + | + | +++ | +++ |
| 3 | ++ | + | 0 | 0 | +++ | ++ |
| 4 | 0 | 0 | 0 | 0 | +++ | 0 |
| 5 | 0 | 0 | 0 | 0 | + | 0 |
| 6 | 0 | 0 | 0 | 0 | 0 | 0 |
| 7 | 0 | 0 | 0 | 0 | 0 | 0 |

TABLE III

| | | | | Influence of the pH upon growth on agar plates | | | | |
|---|---|---|---|---|---|---|---|---|
| pH | M. purpurea ATCC 15835 | M. purpurea NRRL 2953 | M. scalabitana var. rubra ATCC 31435 | M. scalabitana var. sporogenes ATCC 31436 | M. chalcea ATCC 12452 | M. echinospora var. pallida | M. sagamiensis ATCC 21803 | M. sagamiensis ATCC 21949 |
| 7.6 | +++ | +++ | +++ | +++ | +++ | +++ | +++ | +++ |
| 7.2 | +++ | +++ | +++ | +++ | +++ | +++ | +++ | +++ |
| 6.8 | +++ | +++ | +++ | +++ | +++ | +++ | +++ | +++ |
| 6.5 | +++ | +++ | ++ | ++ | +++ | +++ | +++ | +++ |
| 6.1 | + | + | 0 | 0 | +++ | ++ | ++ | ++ |
| 5.8 | 0 | 0 | 0 | 0 | + | 0 | 0 | 0 |
| 5.4 | 0 | 0 | 0 | 0 | 0 | 0 | 0 | 0 |
| 5. | 0 | 0 | 0 | 0 | 0 | 0 | 0 | 0 |

TABLE IV

| | Growth on potato plugs | |
|---|---|---|
| Microorganism: | Potato alone pH 5.4 | Potato - CaCO₃ pH 6.9 |
| M. purpurea ATCC 15835 | Growth: 0 Pigment: 0 | Growth: +++ Pigment: orange later brown |
| M. purpurea NRRL 2953 | Growth: 0 Pigment: 0 | Growth: +++ Pigment: orange, purple spots |
| M. scalabitana var. rubra ATCC 31435 | Growth: 0 Pigment: 0 | Growth: +++ Pigment: dark raspberry red |
| M. scalabitana var. sporgenes ATCC 31436 | Growth: 0 Pigment: 0 | Growth: +++ Pigment: yellow to light orange |
| M. chalcea ATCC 12452 | Growth: ++ Pigment: orange-red | Growth: +++ Pigment: strawberry red |
| M. echinospora var. pallida | Growth: 0 Pigment: 0 | Growth: +++ Pigment: orange turning purple |
| M. sagamiensis ATCC 21803 | Growth: 0 Pigment: 0 | Growth: +++ Pigment: orange | the surface pH became 5.8 and all micromonosporas were able to grow if heavier inoculum was inoculated on the surface. The data resulted are given in Table IV.

Carbohydrate utilization is the most important group of tests necessary for the classification of micromonosporas. They were performed according to the description published by Luedeman. Washed mycelia of all cultures were prepared first and used for inoculation of appropriate sugar agars. Agar medium containing only 0.5% yeast extract and calcium carbonate was used as control.

A single test does not give a completely reliable result. For that reason all tests were repeated in six consecutive generations. For example: glucose agar was inoculated with washed mycelium of M. chalcea. After seven days of incubation at 32° C. the result was recorded and the growing culture was used as inoculum for the second generation on glucose agar. After incubation at 32° C. for seven days the result was recorded and this culture used again as inoculum for the third generation and so on until obtaining the record of six generations of growth on glucose agar. The results obtained are shown in Table V.

Carbohydrate utilization tests are not exactly ideal. There is not a completely negative culture. Even the negative controls represent a scant growth and positive utilization tests represent only increase in size and volume of growth in comparison to the scant growth of the controls. This fact can seriously affect the record because of the personal and highly individual reading that is the basis of evaluation.

Adaptation of strains to certain sugars was noticeable and in some cases the emergence of mutants with different degrees of utilization was observed.

The lactose and d-ribose tests were especially fitting for demonstration of such dissociation of cultures. Other sugars may act similarly but at a lower rate if sufficient number of transfer to transfer to transfer are performed.

Utilization of melibiose is the most important test for classification of micromonosporas. According to the latest (1973) edition of Bergey's Manual (published by the Williams & Wilkins Co., Baltimore, Maryland, USA) all strains utilizing melibiose belong to group A. Micromonospora scalabitana utilizes melibiose.

The next step is raffinose; M. scalabitana does not utilize raffinose.

Spore formation is also used for the classification. M. scalabitana forms spores on longer as well as on shorter monopodial sporophores.

TABLE V

| | Utilization of Carbohydrates | | | | | | |
|---|---|---|---|---|---|---|---|
| Carbohydrate: | M. purpurea ATCC 15835 | M. purpurea NRRL 2953 | M. scalabitana var. rubra ATCC 31435 | M. scalabitana var. sporogenes ATCC 31436 | M. chalcea ATCC 12452 | M. echinospora var. pallida | M. sagamiensis ATCC 21803 |
| Dextrose (Difco) | +++ | +++ | ++ | ++ | +++ | +++ | +++ |
| Sucrose (Difco) | +++ | +++ | +++ | ++ | +++ | +++ | +++ |
| Lactose (E.Merck) | + | + | ++ | +++ | +++ | + | +++ |
| Melibiose (Difco) | 0 | 0 | ++ | ++ | +++ | 0 | +++ |
| Raffinose (Difco) | 0 | 0 | 0 | 0 | ++ | 0 | ++ |
| d-Ribose (E.Merck) | + | + | ++ | ++ | + | + | + |
| Rhamnose (Difco) | 0 | 0 | 0 | 0 | 0 | +++ | + |
| Inosital (Difco) | 0 | 0 | 0 | 0 | 0 | 0 | 0 |
| Mannitol (Difco) | 0 | 0 | 0 | 0 | 0 | 0 | 0 |
| Glycerol (E.Merck) | 0 | 0 | 0 | 0 | 0 | 0 | 0 |
| Soluble starch (Difco) | +++ | +++ | +++ | +++ | +++ | +++ | +++ |
| Potato dextrin (Staley) | +++ | +++ | + | + | +++ | +++ | +++ |

TABLE V-continued

| | | | Utilization of Carbohydrates | | | | |
|---|---|---|---|---|---|---|---|
| Carbohydrate: | M. purpurea ATCC 15835 | M. purpurea NRRL 2953 | M. scalabitana var. rubra ATCC 31435 | M. scalabitana var. sporogenes ATCC 31436 | M. chalcea ATCC 12452 | M. echinospora var. pallida | M. sagamiensis ATCC 21803 |
| Control | 0 | 0 | 0 | 0 | 0 | 0 | 0 |

All these tests would suggest that *M. scalabitana* is a strain of *M. narashinoensis*. Since a culture of this last microorganism was not available, a direct laboratory comparison under controled conditions was not possible.

On table VI the published data on *M. narashinoensis* (Bergey's Manual of Determinative Bacteriology, 1973 Edition) and the laboratory results on *M. scalabitana* are summarized side by side.

There are considerable similarities but also considerable difference between *M. narashinoensis* and *M. scalabitana* and therefore they cannot be considered identical but clearly different, related species.

ANTIBIOTIC PRODUCTION

As pointed out, *Micromonospora scalabitana* grows very well in many culture media. Such media must contain certain assimilable substances as sources of carbon and nitrogen and there must be an adequate supply of oxygen.

Suitable sources of nitrogen are soy proteins, soybean meal, bean meal, pea meal, corn steep liquor, peptones, meat extracts, yeast extracts, casein hydrolysate, nitrate salts, ammonium salts, etc. Many of these substances can serve simultaneously as sources of carbohydrates except, of course, pure chemical salts, as for instance, nitrates and ammonium salts. Many natural carbohydrates can be used as sources of carbon, such as dextrose, sucrose, maltose, lactose, all materials containing starches and dextrines, brewer's malt and many others.

The selected components are dissolved or suspended in deionized water and sterilized in the autoclave. The length of exposure to heat is important to prevent as much as possible the undesirable hydrolysis of the carbohydrates. The pH is also very important and the maintenance of sterility and the purity of the culture used are crucial for good results.

The range of fermentation temperature is wide but the best results for production are between 30° and 35° C. *M. scalabitana* produces gentamicin in the media referred above.

Figure 1:
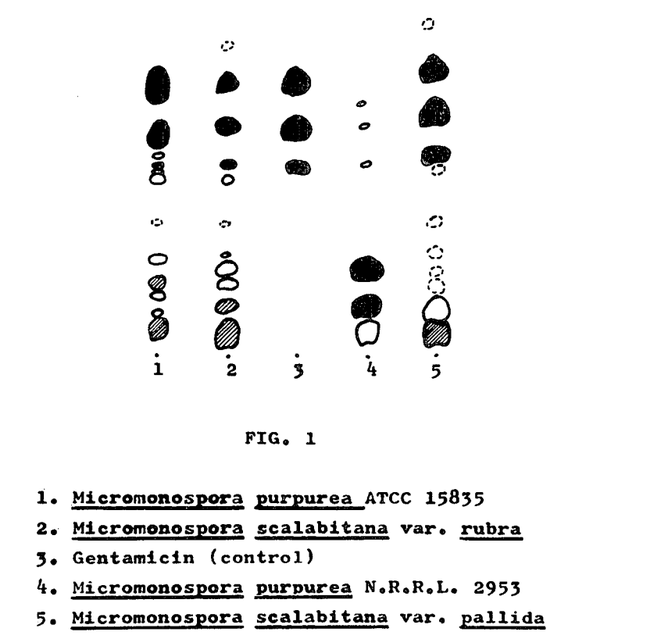

Under the term gentamicin all possible variations of gentamicin are possible, such as gentamicin A, B, the whole group of gentamicins C, antibiotics JI-20A and JI-20B, sisomicin and all others so far described gentamicin-related substances. Since there are great morphological and physiological variations among variants and mutants of *N. scalabitana* there are also great variations in the number, quality and potency of the substances produced. This can be easily demonstrated by paper chromatography or thin layer chromatography. Figure number 1 represents the thin layer chromatography of the gentamicins produced by a few strains tested.

TABLE VI

| | Comparison of M. narashinoensis with M. scalabitana | |
|---|---|---|
| Test | M. narashinoensis | M. scalabitana |
| Spore formation: | Spores spherical or elongate 0.6–1 by 0.9–1.8 Spores develop on branched mycelium within 48 hours, mature spores may be released into medium within 72 hours. | Spores spherical or oblongate 0.8–1.2 by 1.–1.4 Spores develop on branched mycelium, sometimes in 3–4 days, usually in 1–2 weeks and only occasionally we found a few released into medium. |
| Yeast extract-glucose agar: | abundant growth, deep orange color later covered with dark brown spore layer. No soluble pigment | good growth of many colors depending on the variant tested Spore formation of strain with dark hues No soluble pigment |
| Nutrient agar: | Minute orange to tan colored colonies later turning dark when spore formation took place. | Minute colonies, color depending on the variant used. No spore formation |
| Potato plug: | Abundant folded growth, orange at first later turning brown as spore formation occurs. | No growth on potato plug alone. When CaCO₃ is put on the surface, good growth develops. Color and shade develops, or not develops depending on strain tested No spore formation. |
| Gelatin: | liquified | liquified slowly |
| Milk: | digested | digested |
| Nitrates | not reduced | not reduced |
| Ammonium sulfate | utilized moderately | utilizied moderately |
| NaCl tolerance | good 5% | poor −2% good 1% or less |
| Antibiotic produced: | No cardorubin | Gentamicin |

Silica gel plates, type 60, were used and the solvent system was composed of the lower layer of a mixture of methanol-chloroform-28% ammonia (1:1:1). The zones were detected by spraying with a solution of 1 gm of ninhydrin in a mixture of 95% ethanol (50 ml) and glacial acetic acid (10 ml).

Trace elements play an important role in all biological processes because they are essential for some of the enzymatic systems involved in them. Therefore, they are very important in the fermentation process. The importance of half a dozen trace elements in the production of the tetracycline antibiotics by Streptomyces species has been well established by M. A. Petty and T.R.D. McCormick and beneficial effect of cobalt chloride upon the production of *Micromonospora purpurea* was described by W. Charney in U.S. Pat. No. 3,136,704. Various trace elements were tested with *M. scalabitana* using always the same basic medium to reduce to a minimum variations due to the influence of the oligoelements contained in the raw materials used. The most important oligoelement is calcium present as calcium carbonate. All the other elements, when used alone, are beneficial but to a much inferior degree. However, when they are used in combination with calcium carbonate and cobalt chloride they gave a very favourable synergistic effect (see Examples number 4 and 5).

The antibiotic production process consists of several stages. Of those, the most important are: germination stage, preparation of the inoculum, submerged fermentation, one or more stages of extraction and purification and finally, the isolation of the crystalline antibiotic.

The following examples illustrate adequate methods for the production by fermentation of gentamicin according to this invention as well as some brief description of the extraction, purification and isolation stages.

EXAMPLE 1

Fermentation and antibiotic production in shake flasks
Germination Stage: One vial of a lyophylized culture of M. scalabitana was opened and the content mixed under asseptic conditions with 60 ml of broth in an Erlenmeyer flask of 250 ml capacity. The composition of this broth was the following:

| | |
|---|---|
| Corn steep liquor | 1.3% |
| Soluble starch | 2.5% |
| Corn steep liquor | 1.3% |
| Soluble starch | 2.5% |
| Sucrose | 0.1% |
| Calcium carbonate | 0.1% |

All these substances were dissolved or suspended in deionized water, the pH adjusted to 7.2 and distributed into the flasks 60 ml in each one. Sterilization in autoclave at 121° C. for 15 minutes.

The flasks were incubated on a rotary shaker at 32° C. (280 r.p.m., 5 cm stroke) for 3 days. The quality and purity of the cultured flasks was checked. All contaminated or suspicious flasks are eliminated so that only the perfectly pure cultures can be used further.

For a small scale test the germination stage culture can be used as inoculum. For a larger fermentation another step is necessary.

Preparation of inoculum—Pure and well grown cultures of the germination stage are the basis of this step. This inoculum can be prepared in the same broth that was used in the germination stage but other media can be used as well. One such composition is as follows:

| | |
|---|---|
| Beef extract | 0.3% |
| Yeast extract | 0.5% |
| Tryptose | 0.5% |
| Soluble starch | 2.5% |
| Dextrose | 0.1% |
| Calcium carbonate | 0.1% |

Proceed exactly as in the germination stage broth as to preparation, sterilization, etc.

The inoculated flasks are incubated on a rotary shaker (280 r.p.m. at 5 cm stroke) at 32° C. for 3 days. All cultures are checked and only well grown cultures can be used.

Fermentation stage—The composition of the medium is the following:

| | |
|---|---|
| Soybean meal | 3.5% |
| Dextrin | 3.0% |
| Corn starch | 2.0% |
| Potato starch | 0.5% |
| Sucrose | 1.0% |
| Calcium carbonate | 0.05% |

These products are dissolved and/or suspended in deionized water and antifoam (lard oil, for instance) and trace elements are added. The broth is distributed into series of 2 liter Erlenmeyer flasks, measuring 200 ml per flask and sterilized in autoclave at 121° C.

Necessary trace elements: In addition to calcium carbonate, which is most important, only small doses of the following other trace elements are necessary per liter of broth:

| | |
|---|---|
| $CoCl_2 \cdot 6H_2O$ | 1 mg |
| $Ni(CH_3CO_2)_2$ | 1 mg |
| $ZnSO_4 \cdot 7H_2O$ | 5 mg |
| $MnSO_4 \cdot H_2O$ | 5 mg |
| $FeSO_4 \cdot 7H_2O$ | 25 mg |
| $MgSO_4 \cdot 7H_2O$ | 25 mg |

Small variations in the quantities necessary for the best results can be demonstrated when media are prepared from different sources of raw materials because there are variations in their content of trace elements.

For good growth of *M. scalabitana* it is necessary to prepare the broth in a way slightly different from general custom. *M. scalabitana* does not grow well if dextrin and starches are hydrolysed. Therefore, the pH of the fermentation medium before fermentation is not adjusted prior to sterilization but afterwards by pipetting 10% sodium hydroxide in adequate quantity. Ten percent volume is used as inoculum, i.e., 20 ml of prepared inoculum per 200 ml of fermentation broth in each flask.

All inoculated flasks are placed on a rotary shaker (150-180 r.p.m.) in an incubator room at 32° C. for 5-7 days. Small samples can be occasionally removed asseptically.

Microscopical examination, pack cell volume and antibiotic titer are checked and recorded. At the end of incubation there was a titer between 400 and 500 micrograms of gentamicin activity per ml of broth produced.

Extraction: The pooled broth is acidified to pH 2.0 using 12 N sulfuric acid, stirring it for 30-40 minutes. After admixing a perlitic filter aid such as Dicalite 478R (a product of Dicalite Española, S.A., Barcelona, Spain), the mycelium is removed together with the filter aid by filtration and discarded. The pH of the filtered broth is adjusted to 8.0 with 6 N Sodium hydroxide and the broth passed through a glass column filled with a weak cationic ion exchange resin such as Amberlite IRC-50 (a product of the Rohm & Hass Co., Philadelphia, Pennsylvania, U.S.A.). The active antibiotics are adsorbed and the efluent can be discarded. The crude antibiotic may be eluted from the column with 1 N aqueous ammonia. Purification of the crude product may be carried out by adsorption on a silica gel column, elution with chloroform-methanol-ammonia and concentrating the various fractions in vacuum.

The final purified product conforms with the specifications of the U.S. Food and Drug Administration for gentamicin sulfate. The ratio of the various components may be determined by thin layer chromatography as described above. FIG. 1 shows the t.l.c. results of the crude antibiotic isolated from *M. scalabitana* var. rubra (number 2) and from *M. scalabitana* var. pallida (number 5).

EXAMPLE II

Fermentation in 10-liter laboratory fermentors

The germination stage is prepared exactly as described in Example I. One liter of inoculum is necessary for the inoculation of a ten-liter fermenter. Therefore, a sufficient number of Erlenmeyer flasks must be prepared with the composition of the germination broth shown in Example I, inoculated and incubated on a rotary shaker at 32° C. for 3 days.

In the meantime a small laboratory fermenter of 10 l is prepared and filled with the following broth:

| | |
|---|---|
| Soybean meal | 350 gm |
| Potato dextrine | 250 gm |
| Corn starch | 150 gm |
| Potato starch | 100 gm |
| Sucrose | 100 gm |
| $CaCO_3$ | 5 gm |
| $CoCl_2 \cdot 6H_2O$ | 8 mg |
| $Ni(CH_3CO_2)_2$ | 8 mg |
| $ZnSO_4 \cdot 7H_2O$ | 50 mg |
| $MnSO_4 \cdot H_2O$ | 50 mg |
| $MgSO_4 \cdot H_2O$ | 250 mg |
| $FeSO_4 \cdot 7H_2O$ | 250 mg |

All the ingredients are suspended and/or dissolved directly in the jar of the 10-liter fermenter, 20 ml of lard oil is added as antifoam, the cover closed tightly and sterilized in autoclave at 121° C. for one hour. The pH is adjusted only after sterilization adding 25 ml of 10% sodium hydroxide. This way the hydrolysis of the ingredients will be minimal.

The loaded fermenter containing the sterile broth is placed in its water bath, the stirring mechansim is connected, aeration started and when the temperature reaches 34° C., the fermenter is inoculated under asseptic conditions by adding one liter of the prepared inoculum.

The fermentation at 34° C. is prolonged for 5 to 7 days checking occasionally the the quality of growth, microscopic examination, purity of culture and of course checking and recording the titer of produced antibiotics.

When the titer reached 450 μgm per ml, the fermentation was terminated and the antibiotic extracted, purified and evaluated as it was described in Example I.

EXAMPLE III

Fermentation in 150-liter fermenters

The experiment was started as in the two previous examples.

A germination stage culture is prepared and after 3 days of incubation in the rotary shaker it is used to prepare the inoculum.

For the second stage, two steps will be needed. In the first step a volume of one liter of culture will be prepared as in Example II, using the following broth in skake flasks:

| | |
|---|---|
| Beef extract | 0.3% |
| Yeast extract | 0.5% |
| Tryptose | 0.5% |
| Soluble starch | 2.5% |
| Dextrose | 0.1% |
| Calcium carbonate | 0.1% |

The pH is adjusted to 7.2, 20° ml portions of the broth are distributed into 2-liter Erlenmeyer flasks and sterilized in the autoclave at 121° C. for 25 minutes.

The inoculated flasks are incubated on a rotary shaker (150–180 r.p.m.) for 3 days. After checking for quality and purity the volume is pooled under asseptic conditions and is ready to be used for inoculation of a 10-liter fermentor in which the inoculum for the large fermentor will be prepared.

The medium for the 10-liter fermentor can be as follows:

| | |
|---|---|
| Sucrose | 3.0% |
| Solid corn steep | 1.5 to 2.0% |
| Calcium carbonate | 0.7% |
| Ammonium sulfate | 0.2% |
| Soybean meal | 1.0% |
| Lard oil | 20 ml |

The preparation is carried out directly in the small fermentor using deionized water, adjusting the pH to 7.2 and sterilizingin autoclave at 121° C. for one hour.

The fermentor is placed in its thermostated bath and, when the inside temperature is 34° C., one liter of seed culture prepared in step number one is added under asseptic conditions. The incubation takes place at 34° C. with constant stirring and aeration.

In the meantime the large fermentor is prepared, filled with fermentation broth and sterilized.

The composition of the fermentation broth, is as follows:

| | |
|---|---|
| Soybean meal | 5.0 kg |
| Potato dextrin | 3.5 kg |
| Corn starch | 1.0 kg |
| Potato starch | 1.0 kg |
| Sucrose | 1.5 kg |
| $CaCO_3$ | 0.8 kg |
| $CoCl_26H_2O$ | 120 mg |
| $Ni(CH_3CO_2)_2$ | 100 mg |
| $ZnSO_4 \cdot 7H_2O$ | 750 mg |
| $MnSO_4 \cdot H_2O$ | 750 mg |
| $MgSO_4 \cdot 7H_2O$ | 3.75 gm |
| $FeSO_4 \cdot 7H_2O$ | 3.75 gm |

The components are dissolved and/or suspended in 150 liters of deionized water, not more than 2% of antifoam is added and the contents sterilized under pressure. The pH is adjusted after sterilization adding enough 40% sodium hydroxide to reach pH 7.4–7.5.

The fermentor is cooled to 34° C. and inoculated by adding at least 10 liters (preferably 15 liters) of the inoculum prepared in 10-liter fermentors.

The fermentation is continued for 5 to 7 days at 34° C. Once a day a sample is taken under asseptic conditions for the necessary checking and evaluation of growth, purity and antibiotic potency. The fermentation was discontinued when the potency reached 475 μgm/ml.

The broth was cooled to 20° C., the pH adjusted to 1.5–2.5 with oxalic acid under constant stirring, 1.5–2.0% of Dicalite 478R added and the mycelium and filter aid removed by filtration. After neutralization of the filtered broth with 6 N sodium hydroxide at 15° C. it was passed through a battery of ion exchange columns filled with Amberlite IRC-50 in the sodium cycle. After washing it with water the columns were eluted with 4 N sulfuric acid. Various fractions were combined, the pH adjusted to 5.0–5.5 with triethylamine, treated with activated carbon and poured into eight volumes of methanol. The crude gentamicin sulfate had a potency of 400 μgm/mg and was purified by dissolving in water (100.000 μgm/ml), treating with activated carbon and adsorbing the activity in a set of glass columns containing a finely ground weak cationic ion exchanger like Amberlite CG-50 in the ammonium cycle. Elution was carried out with 0.1–0.5 N ammonia and the fractions containing the $C_{1a}$, $C_1$ and $C_2$ components combined, concentrated under vacuum to one tenth of the original volume, the pH adjusted to 5.0–5.5 with 5% sulfuric acid and precipitated with methanol. The dried product had an activity of 650 μgm/mg.

EXAMPLE IV

Influence of various trace elements upon gentamicin production in shake flasks

Various trace elements were tested with *M. scalabitana* var. rubra in a simple broth in which there was soybean meal 3%, dextrin 4%, dextrose 0.5% dissolved in deionized water. This composition was used as the basic medium to which various salts, singly and in combination were added. After sterilization in autoclave at 121° C. for 15 minutes every flask was inoculated using one ml of a fresh broth culture of *M. scalabitana* var. rubra, incubated on a rotary shaker (280 r.p.m., 5 cm stroke) at 32° C. for seven days. Then all flasks were evaluated, antibiotic titers established and the results tabulated in Table VII.

From these data it is concluded that really many salts in small amounts are important for gentamicin production by *M. scalabitana* var. rubra. The most important is calcium carbonate. All other chemicals, when used alone, were beneficial but their effect was much inferior. However, when they were used in combination with calcium carbonate and cobalt chloride they gave a very favourable synergistic effect.

EXAMPLE V

As a demonstration of the importance of multiple trace elements for the successful production of gentamicin, the following experiment was carried in 10 liter fermentors. One fermentor marked A was used as control and was filled with the following broth:

| | |
|---|---|
| Soybean meal | 300 gm |
| Corn starch | 400 gm |
| Dextrose | 50 g |
| Calcium carbonate | 5 g |
| Cobalt chloride | 8 mg |
| Deionized water | 10 liters |

After adding antifoam, the whole fermentor was sterilized in autoclave for one hour at 121° C. The pH was adjusted after sterilization adding asseptically 5 ml of 40% sodium hydroxyde.

A second fermentor, marked B, was prepared the same way with exactly the same ingredients in the same amounts. The only difference was the presence of additional trace elements which were added in the following amounts:

TABLE VII

Basal medium plus trace elements (per 100 ml of broth)

| Medium | Trace elements: | Packed cell volume | Titer: |
|---|---|---|---|
| 1 | 0 | 1.6 | 22 |
| 2 | 50mg $CaCO_3$ | 2.3 | 82 |
| 3 | 0.1mg $COCl_2 . 6H_2O$ | 1.8 | 54 |
| 4 | 0.1mg $Ni(CH_3CO_2)_2$ | 1.9 | 30 |
| 5 | 2.5mg NaCl | 1.8 | 42 |
| 6 | 2.5mg $MgSO_4 . 7H_2O$ | 1.7 | 48 |
| 7 | 2.5mg $FeSO_4 . 7H_2O$ | 1.8 | 32 |
| 8 | 0.5mg $ZnSO_4 . 7H_2O$ | 1.8 | 36 |
| 9 | 0.5mg $MnSO_4 . H_2O$ | 1.9 | 30 |
| 10 | 2.5mg $Na_2S_2O_4$ | 1.8 | 32 |
| 11 | 2.5mg $K_2HPO_4$ | 1.8 | 45 |
| 12 | 50mg $CaCO_3$ + 0.1mg $CoCl_2 . 6H_2O$ | 2.4 | 154 |
| 13 | 50mg $CaCO_3$ + 0.1mg $CoCl_2 . 6H_2O$ + +2.5mg $FeSO_4 . 7H_2O$ | 2.7 | 258 |
| 14 | 50mg $CaCO_3$ + 0.1mg $CoCl_2 . 6H_2O$ + +0.5mg $ZnSO_4 . 7H_2O$ | 2.7 | 245 |
| 15 | 50mg $CaCO_3$ + 0.1mg $CoCl_2 . 6H_2O$ + +0.5mg $MnSO_4 . H_2O$ | 3.— | 238 |
| 16 | 50mg $CaCO_3$ + 0.1mg $CoCl_2 . 6H_2O$ + +0.1mg $Ni(CH_3CO_2)_2$ | 2.8 | 258 |
| 17 | 50mg $CaCO_3$ + 0.1mg $CoCl_2 . 6H_2O$ + +0.1mg $Ni(CH_3CO_2)_2$ + +2.5mg $FeSO_4 . 7H_2O$ | 2.6 | 328 |
| 18 | 50mg $CaCO_3$ + 0.1mg $CoCl_2 . 6H_2O$ + +0.1mg $Ni(CH_3CO_2)_2$ + 0.5mg $MnSO_4 . H_2O$ | 2.5 | 293 |

| | |
|---|---|
| Ni $(CH_3CO_2)_2$ | 8 mg |
| $ZnSO_4 . 7H_2O$ | 50 mg |
| $MnSO_4 . H_2O$ | 50 mg |
| $MgSO_4 . 7H_2O$ | 250 mg |
| $FeSO_4 . 7H_2O$ | 250 mg |

The addition of antifoam, sterilization and adjustment of the pH were done exactly as in the fermentor A.

Both fermentors were inoculated with the same volume of 500 ml of a 3-day old culture of *M. scalabitana* var. rubra and were incubated for 6 days at a temperature of 34° C. with constant stirringd and aeration.

When the fermentation was terminated the control fermentor A (with calcium carbonate and cobalt chloride) had a titer of 358 μgm while fermentor B (with calcium carbonate, cobalt chloride plus all other trace elements) had a titer of 488 μgm/ml.

I claim:

1. A process for the preparation of the gentamicins which comprises the cultivation of a new species, *Micromonospora scalabitana*, or mutants thereof, under aerobic conditions, in a medium containing adequate sources of assimilable carbon and nitrogen and trace elements.

2. A process according to claim 1, wherein the microorganism is *Micromonospora scalabitana,* var. rubra A.T.C.C. 31435.

3. A process according to claim 1 wherein the antibiotic produced is a mixture of the three gentamicins $C_1$, $C_2$ and $C_1a$.

4. A process according to claim 1 wherein the sources of carbon and nitrogen are, respectively, selected from the group consisting of dextrose, sucrose, lactose, dextrin, starch, starch-containing materials and soybean meal, bean meal, pea meal, corn steep liquor and ammonium sulfate.

5. A process according to claim 1 wherein there is employed calcium carbonate 0.05% and a synergistic mixture of soluble salts of trace elements consisting of 0.0001% of nickel acetate, 0.0001% cobalt chloride, 0.0005% zinc sulfate, 0.0005% manganese sulfate, 0.0025% magnesium sulfate and 0.0025% ferrous sulfate.

6. A process according to claim 4 wherein there is employed calcium carbonate 0.05% and a synergistic mixture of soluble salts of trace elements is present and consisting of 0.0001% of nickel acetate, 0.0001% cobalt chloride, 0.0005% zinc sulfate, 0.0005% manganese sulfate, 0.0025% magnesium sulfate and 0.0025% ferrous sulfate.

* * * * *